United States Patent

Kamrat

[11] Patent Number: 5,563,737
[45] Date of Patent: Oct. 8, 1996

[54] ARRANGEMENT FOR CLEANING AN OPTICAL WINDOW IN A PROCESS

[75] Inventor: Esko Kamrat, Vantaa, Finland

[73] Assignee: Janesko Oy, Vantaa, Finland

[21] Appl. No.: 390,374

[22] Filed: Feb. 16, 1995

Related U.S. Application Data

[63] Continuation of Ser. No. 153,790, Nov. 17, 1993, abandoned, which is a continuation of Ser. No. 939,993, Sep. 3, 1992, abandoned.

[30] Foreign Application Priority Data

Sep. 18, 1991 [FI] Finland ................................ 914385

[51] Int. Cl.⁶ ............................. G02B 7/18; G01N 21/41
[52] U.S. Cl. .......................... 359/509; 359/507; 356/128; 356/136
[58] Field of Search .................................. 359/507–509, 359/511–513, 894; 356/128, 134–136, 442, 438–439

[56] References Cited

U.S. PATENT DOCUMENTS

| 3,027,644 | 4/1962 | Piscitelli | 359/509 |
|---|---|---|---|
| 3,516,723 | 6/1970 | Guier | 359/509 |
| 3,625,437 | 12/1971 | Garrigou | 239/469 |
| 3,628,867 | 12/1971 | Brady | 356/136 |
| 3,861,198 | 1/1975 | Shea | 359/509 |
| 4,172,428 | 10/1979 | Pariset | 359/894 |
| 4,281,646 | 8/1981 | Kinoshita | 359/509 |
| 4,516,288 | 5/1985 | Fizyta et al. | 239/284.1 |
| 4,658,113 | 4/1987 | Vingerling | 359/509 |
| 4,874,243 | 10/1989 | Perren | 356/342 |

FOREIGN PATENT DOCUMENTS

| 3721370 | 1/1988 | European Pat. Off. | 359/509 |
|---|---|---|---|
| 48102 | 2/1981 | Japan | 359/509 |

Primary Examiner—Thong Nguyen
Attorney, Agent, or Firm—Fitch, Even, Tabin & Flannery

[57] ABSTRACT

An arrangement for cleaning an optical window in an instrument such as a refractometer located in-line in a continuous or batch process, comprising a nozzle for spraying under high pressure a harmless cleaning medium onto the optical window. The nozzle is firmly fixed in a nozzle frame, the frame itself being firmly attached to the instrument in the vicinity of the optical window. The nozzle is recessed in the frame. The invention achieves cleaning of the optical window without mechanical parts or strong solvents, and does not require removal of the instrument from its in-line position.

6 Claims, 2 Drawing Sheets

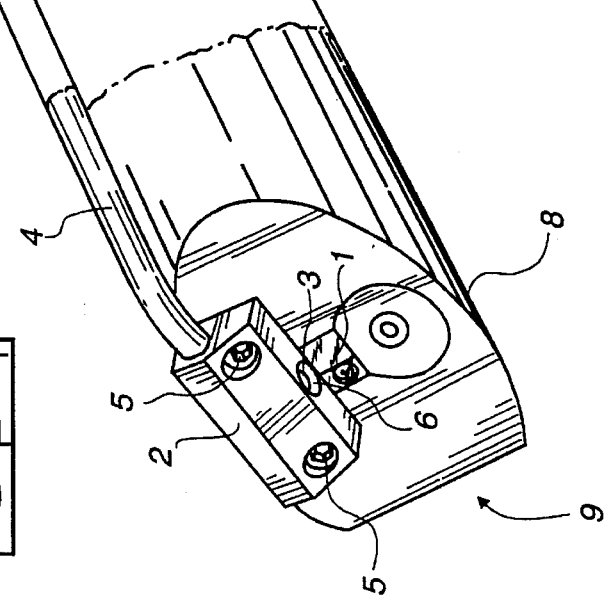
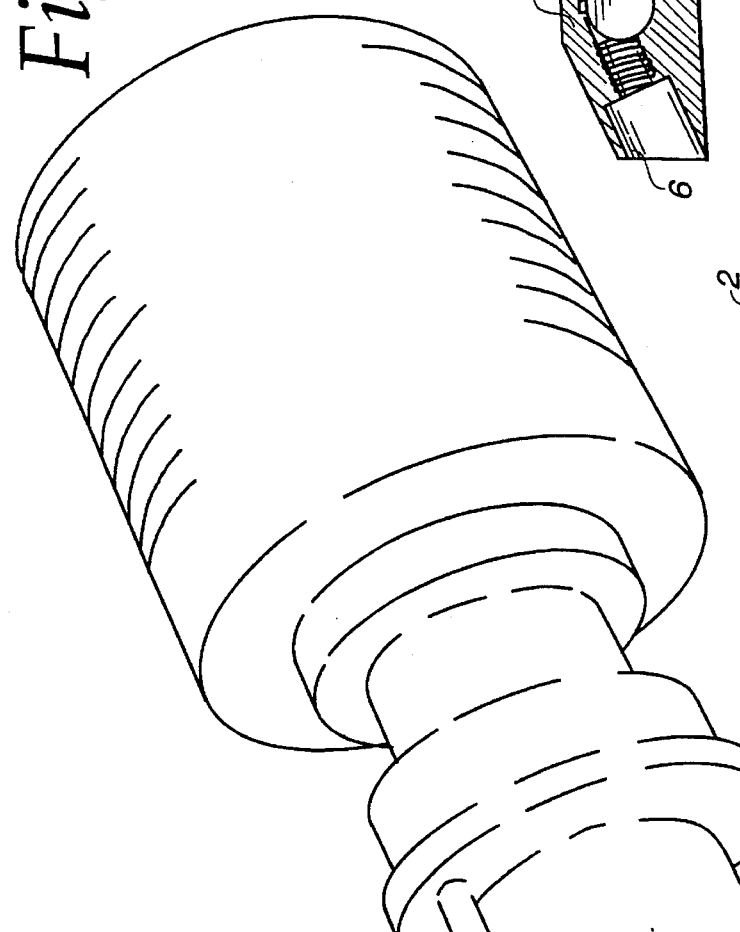
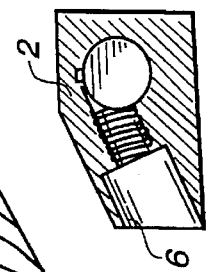
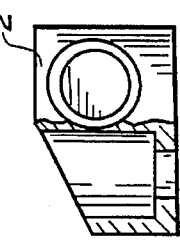
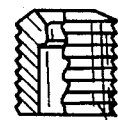
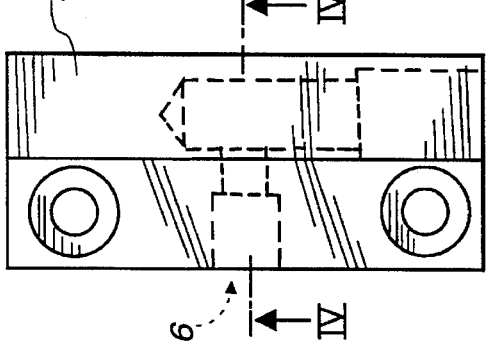

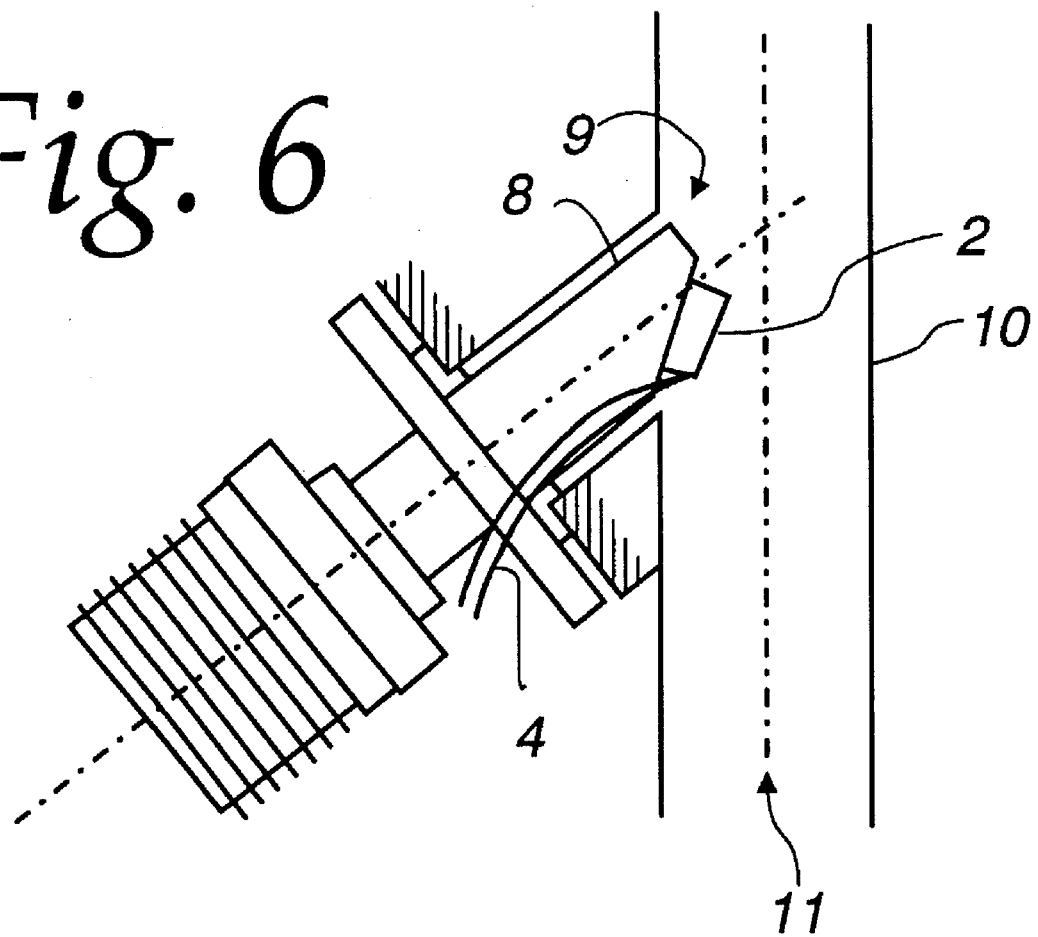

ARRANGEMENT FOR CLEANING AN OPTICAL WINDOW IN A PROCESS

This application is a continuation of application Ser. No. 08/153,790, filed Nov. 17, 1993, now abandoned, which is a continuation of application Ser. No. 07/939,993, filed Sep. 3, 1992, now abandoned.

BACKGROUND OF THE INVENTION

1. Field of the Invention

The invention relates to an arrangement for cleaning an optical window in a process, comprising means for conducting a cleaning medium to an optical window that is to be arranged in connection with a flow or the like provided in the process, the means comprising a nozzle arranged to direct a medium jet onto the surface of the optical window.

2. Description of the Related Art

Optical windows in a process are utilised today in many different industrial fields, such as food industry, paper industry, chemical industry and different research projects. An optical window may be a part in different measuring devices, such as process refractometers, which are used to determine the concentration of a solution. In a process refractometer an optical window may be provided e.g. by a prism. An example for such process refractometers is Process Refractometer PR-01 manufactured by K-Patents Oy.

The problem with optical windows arranged in a process is that they become dirty, whereby the measuring result is inaccurate and even incorrect. An example for solutions previously used in the field is a nozzle which is arranged to direct e.g. a vapour or water jet onto the surface of the optical window. Another example is the use of mechanical cleaning means, such as wipers. However, the above solutions are not sufficiently effective in difficult conditions. A drawback with nozzle solutions is e.g. their poor directability and their sensitivity to the effects of the flow to be measured. A drawback with mechanical cleaning means is their sensitivity to impurities, whereby they operate unreliably.

On account of the above new kinds of solution have been developed in the field for reliably cleaning of an optical window even in difficult conditions. An example for such devices is an apparatus arranged in the side of the wall of a process tube that is opposite to the measuring end, whereby the cleaning means are situated at the corresponding place as the optical window at the measuring end but on the opposite wall of the process tube. The cleaning means are transferred across the process tube by means of pressurised air to be in contact with the optical window at the measuring end such that the cup-shaped member of the cleaning means surrounds the optical window. In the following step hydrochloric acid is fed into the cup-shaped member for a predetermined time. The hydrochloric acid is intended to clean the optical window. When the cleaning step has been completed, the cup-shaped member is transferred back to the initial position. The above apparatus is intended to operate particularly in measurings carried out in connection with green liquor.

A drawback with the above solution is above all its complexity as well as moving mechanisms that are easily jammed when the mechanisms become dirty. Also, the use of an acid certainly does not facilitate the use of the apparatus since the use of an acid is problematic with regard to the environment and safety at work. A further drawback is the price, which is rather high due to the complexity of the apparatus. Also the operating costs of said known apparatus are high primarily due to the great need for service.

SUMMARY OF THE INVENTION

The object of the invention is to provide an arrangement by means of which the drawbacks of the prior art can be eliminated. This is achieved by an arrangement according to the invention, which is characterised in that the nozzle is arranged in the immediate vicinity of an optical window by fixing it firmly with small tolerances to the holding block of the optical window, whereby a medium jet can be directed accurately onto the surface of the optical window.

The primary advantage of the invention is that effective cleaning of an optical window without problematic moving mechanisms and strong solvents can be carried out. It is also advantageous that the apparatus is simple, wherefore the manufacturing and operating costs are not so high. Owing to the simple structure, the arrangement according to the invention operates reliably. A further advantage is the small size of the arrangement, wherefore no practical problems arise when the arrangement is positioned. The positioning of the arrangement in the process is also facilitated by the fact that the medium is completely harmless.

BRIEF DESCRIPTION OF THE DRAWINGS

In the following, the invention will be described in greater detail with the aid of an advantageous embodiment presented in the attached drawing, wherein FIG. 1 shows a perspective view of an arrangement according to the invention in connection with a process refractometer, FIGS. 2 to 4 show views of the frame member of the arrangement according to the invention from different directions, FIG. 5 shows a side view of the nozzle of the arrangement according to the invention, and FIG. 6 is a side view of the process refractometer of FIG. 1 with its end extending through the wall of a process tube.

DESCRIPTION OF THE PREFERRED EMBODIMENTS

FIG. 1 shows an arrangement according to the invention arranged in connection with a process refractometer. In the example according to the figure the process refractometer is Process Refractometer PR-01 manufactured by K-Patents Oy. The number 1 indicates an optical window, which in the embodiment of FIG. 1 is a prism.

The structure and operation of the process refractometer shown in FIG. 1 are quite conventional technology to one skilled in the art, wherefore these features are not presented in greater detail herein. With respect to the structure and operation of the process refractometer it is here pointed out quite generally that the apparatus is arranged, for example, in the wall of a process tube 10 (FIG. 6) such that the end 9 of the apparatus where the optical window 1 is found is in contact with the substance 11, such as green liquor, flowing in the tube 10. Inside the apparatus is a light source from which light is conducted to the optical window 1 such that deviation and total reflection of light beams occur, depending on the concentration of the substance 11 flowing in the tube 10, on the surface of the optical window 1 shown in FIG. 1 and being in contact with the substance 11 flowing in the tube. The data concerning the angle of total reflection are converted into electrical form by the electronics of the apparatus and further taken outside the device e.g. for controlling or storage.

In the figures the number 2 indicates a frame member of the arrangement. FIGS. 2 to 4 show views of the frame member 2 from different directions. The number 3 in the figures indicates a nozzle and the number 4 indicates a tube for conducting the medium. The nozzle 3 is fixed to the frame member 2 and one end of the tube 4 is also fixed to the frame member 2. The other end of the tube 4 is connected to a medium source, which is not shown in the figures.

According to the principle idea of the invention the optical window 1 is cleaned by means of an apparatus consisting of a nozzle 3, a frame member 2 and a tube 4 by positioning the nozzle 3 in the immediate vicinity of the optical window and by directing a high pressure medium jet onto the surface of the optical window 1 by means of the nozzle 3. The medium can be, for example, pressurised water. A pressurised medium jet cleans the surface of the optical window 1 mechanically as it hits the surface. In the prior art the optical window is cleaned, for example, chemically. The jet is directed onto the surface of the optical window 1 at a suitable angle, which may vary according to the situation. An example for a suitable angle is 25°.

The nozzle 3 is fixed to the immediate vicinity of the optical window 1 by fixing it firmly with small tolerances to the holding block 8 of the optical window 1. The medium jet can then be directed accurately onto the surface of the optical window. As a result of firm fixing and small tolerances, e.g. accuracy of a machine tool, the jet is rendered sufficiently accurate and the accuracy can be retained sufficiently stable even in difficult situations.

In the embodiment shown in the figures the nozzle 3 is arranged firmly in a refractometer, i.e. in the same apparatus as the optical window 1. This is very significant, as stated above, since the pressurised medium jet can then be directed correctly with very small tolerances and the cleaning action can be optimized. In the embodiment of the figures the nozzle 3 is fixed to the frame member 2 and, correspondingly, the frame member 2 is fixed to the immediate vicinity of the optical window in the refractometer. The nozzle 3 can be fixed to the frame member 2 e.g. by threading and, correspondingly, the frame member can be fixed with screws 5.

It is particularly advantageous to arrange the nozzle 3 in a recess 6 such that the edges of the recess 6 protect the nozzle 3 from the flow provided in the process. This is essential since, protected from the flow of the process substance to be measured, the pressurised medium jet is capable of achieving the size of the optical window and the optical window 1 can be covered fully and effectively with the pressurised medium jet. This has a clear effect on the result of the cleaning action. It is to be noted that the substance employed in the process may have high viscosity and the amount of flow may be great, whereby the flow may, without any special arrangements, essentially disturb the pressurised medium jet. In the embodiment shown in the figures the recess 6 is provided by boring. In this embodiment the nozzle 3 is positioned at the bottom of the recess.

The embodiment shown in the figures is not intended to restrict the invention in any way but the invention can be modified quite freely within the scope of the claims. Thus it is clear that the arrangement according to the invention or parts thereof need not necessarily be identical to those shown in the figures but also other kinds of solution may be used. The nozzle and the frame member need not necessarily be provided as separate parts but the nozzle can be provided, e.g., by machining, in the frame member, and the frame member can be provided as a permanent part of a refractometer or another corresponding device, and so on. The pressure of the pressurised medium may vary as necessary, the only essential matter being that the pressure of the cleaning medium is high, as stated above. An example for this is a pressure of 50 to 100 bar, whereby the mechanical effect and cleaning capacity of the jet are good. The high medium pressure can be generated in any manner known per se.

I claim:

1. An arrangement for cleaning an optical window having a surface in substantially full contact with a process fluid flow to be measured through the window, the arrangement comprising:

a holding block for mounting said window to dispose the surface of the optical window in substantially full contact with the process fluid flow to be measured, a nozzle frame securely attached to the holding block, a nozzle securely affixed to the nozzle frame, and disposed to direct a jet of cleaning medium through said process fluid flow onto the surface of the optical window, said nozzle being arranged in the immediate vicinity of the optical window by fixing it firmly with small tolerances to the nozzle frame, to direct said jet of cleaning medium accurately onto the surface of the optical window through the process fluid flow.

2. An arrangement according to claim 1, wherein the jet of cleaning medium to be directed onto the surface of the optical window by means of the nozzle is a high pressure jet, the pressure being in the range from 50 bar to 100 bar.

3. An arrangement according to claim 2, wherein the nozzle is arranged in a recess having edges such that the edges of the recess protect the nozzle from the flow.

4. An arrangement according to claim 3, wherein the recess is provided by boring and that the nozzle is arranged at the bottom of the recess.

5. An arrangement according to claim 1, wherein the nozzle is arranged in a recess of the nozzle frame having edges such that the edges of the recess protect the nozzle from the flow.

6. An arrangement according to claim 5, wherein the recess is provided by boring and that the nozzle is arranged at the bottom of the recess.

* * * * *